US009079550B2

(12) United States Patent  (10) Patent No.: US 9,079,550 B2
Fabian et al.  (45) Date of Patent: Jul. 14, 2015

(54) SPINE SURGERY METHOD AND INSTRUMENTATION

(75) Inventors: Henry F. Fabian, Steamboat Springs, CO (US); Larry A. Cicoretti, Poland, OH (US)

(73) Assignee: Vertebration, Inc., Powell, OH (US)

( * ) Notice: Subject to any disclaimer, the term of this patent is extended or adjusted under 35 U.S.C. 154(b) by 757 days.

(21) Appl. No.: 13/269,643

(22) Filed: Oct. 10, 2011

(65) Prior Publication Data

US 2012/0029645 A1 Feb. 2, 2012

Related U.S. Application Data

(62) Division of application No. 11/756,168, filed on May 31, 2007, now Pat. No. 8,070,754.

(51) Int. Cl.
| | |
|---|---|
| *A61B 17/58* | (2006.01) |
| *A61B 17/60* | (2006.01) |
| *A61F 2/00* | (2006.01) |
| *B60R 19/18* | (2006.01) |
| *B60K 13/02* | (2006.01) |
| *B60K 13/04* | (2006.01) |
| *B60R 19/50* | (2006.01) |
| *B60Q 1/26* | (2006.01) |

(52) U.S. Cl.
CPC ............ *B60R 19/18* (2013.01); *B60K 13/02* (2013.01); *B60K 13/04* (2013.01); *B60Q 1/2626* (2013.01); *B60Q 1/2653* (2013.01); *B60R 19/50* (2013.01); *B60R 2019/1886* (2013.01); *Y10T 29/49826* (2015.01)

(58) Field of Classification Search
USPC ........................................................ 606/99
See application file for complete search history.

(56) References Cited

U.S. PATENT DOCUMENTS

| | | |
|---|---|---|
| 5,439,464 A | 8/1995 | Shapiro |
| 5,505,732 A | 4/1996 | Michelson |
| 5,772,661 A | 6/1998 | Michelson |
| 5,785,647 A | 7/1998 | Tompkins et al. |
| 6,080,155 A | 6/2000 | Michelson |
| 6,093,207 A | 7/2000 | Pisharodi |

(Continued)

FOREIGN PATENT DOCUMENTS

WO  WO 02/05733  1/2002

OTHER PUBLICATIONS

Disc Orthopaedic Technologies to Introduce B-Twin Expandable Spinal Fusion System at NASS, by N.J. Monroe, dated Sep. 26 (no year given), article from PRNewswire, copyright 1996-2006 PR Newswire Association LLC, webpage (http://www.prnewswire.com/cgi-bin/stories.pl?ACCT=104&STORY=/www/story//09-26-2005/0004131865&EDATE=), USA.

(Continued)

*Primary Examiner* — Nicholas Woodall
*Assistant Examiner* — Christine Nelson
(74) *Attorney, Agent, or Firm* — Timothy D. Bennett; Emerson Thomson Bennett

(57) ABSTRACT

Surgical instrumentation for use in placing an implant into a disc space between a pair of spinal vertebrae may include: (a) a distractor having a distal end that may be placed into the disc space between the pair of spinal vertebrae; (b) an inserter for use in moving the implant toward the disc space between the pair of spinal vertebrae; and, (c) a distractor/inserter rail/groove interconnection that interconnects the distractor and the inserter for relative movement thereby.

13 Claims, 18 Drawing Sheets

(56) References Cited

U.S. PATENT DOCUMENTS

| | | | |
|---|---|---|---|
| 6,159,214 | A | 12/2000 | Michelson |
| 6,193,757 | B1 | 2/2001 | Foley et al. |
| 6,228,022 | B1 | 5/2001 | Friesem et al. |
| 6,283,966 | B1 | 9/2001 | Houfburg |
| 6,332,887 | B1 | 12/2001 | Knox |
| 6,395,031 | B1 | 5/2002 | Foley et al. |
| 6,471,724 | B2 | 10/2002 | Zdeblick et al. |
| 6,514,260 | B1 | 2/2003 | Zdeblick et al. |
| 6,524,318 | B1 | 2/2003 | Longhini et al. |
| 6,554,836 | B2 | 4/2003 | Michelson |
| 6,565,574 | B2 | 5/2003 | Michelson |
| 6,575,981 | B1 | 6/2003 | Boyd et al. |
| 6,648,895 | B2 | 11/2003 | Burkus et al. |
| 6,652,533 | B2 | 11/2003 | O'Neil |
| 6,695,851 | B2 | 2/2004 | Zdeblick et al. |
| 6,712,819 | B2 | 3/2004 | Zucherman et al. |
| 6,712,825 | B2 | 3/2004 | Aebi et al. |
| 6,723,096 | B1 | 4/2004 | Dorchak et al. |
| 6,740,087 | B2 | 5/2004 | Knox |
| 6,743,234 | B2 | 6/2004 | Burkus et al. |
| 6,755,841 | B2 | 6/2004 | Fraser et al. |
| 6,761,723 | B2 | 7/2004 | Buttermann et al. |
| 6,770,074 | B2 | 8/2004 | Michelson |
| 6,814,737 | B2 | 11/2004 | Cauthen |
| 6,824,565 | B2 | 11/2004 | Muhanna et al. |
| 6,830,570 | B1 | 12/2004 | Frey et al. |
| 6,830,574 | B2 | 12/2004 | Heckele et al. |
| 6,833,006 | B2 | 12/2004 | Foley et al. |
| 6,863,673 | B2 | 3/2005 | Gerbec et al. |
| 6,923,814 | B1 | 8/2005 | Hildebrand et al. |
| 7,060,073 | B2 | 6/2006 | Frey et al. |
| 7,070,598 | B2 | 7/2006 | Lim et al. |
| 7,081,120 | B2 | 7/2006 | Li et al. |
| 7,087,055 | B2 | 8/2006 | Lim et al. |
| 7,128,760 | B2 | 10/2006 | Michelson |
| 7,163,561 | B2 | 1/2007 | Michelson |
| 2002/0045904 | A1 | 4/2002 | Fuss et al. |
| 2002/0045944 | A1 | 4/2002 | Muhanna et al. |
| 2004/0230100 | A1 | 11/2004 | Shluzas |
| 2004/0236331 | A1 | 11/2004 | Michelson |
| 2004/0249388 | A1 | 12/2004 | Michelson |
| 2008/0300601 | A1 | 12/2008 | Fabian et al. |

OTHER PUBLICATIONS

B-Twin Expandable Spinal System, web page (http://www.disc-o-tech.com/Articles/Article.asp?CategoryID=4&ArticleID=74), no date given.

Patent Cooperation Treaty, International Search Report, Date completed; Nov. 7, 2006, p. 1-7, ISA, European Patent Office, P.B. 5818 Patentlaan 2 NL-2280 HV Rijswijk.

Patent Cooperation Treaty, International Preliminary Report, Date completed: Dec. 13, 2007, p. 1-20. International Preliminary Examining Authority, European Patent Office—Gitschiner Str. 103 D-11958 Berlin.

Patent Cooperation Treaty, Written Opinion of the International Searching Authority, p. 1-9, ISA, European Patent Office—Gitschiner Str. 103 D-10958 Berlin.

SPINE SURGERY METHOD AND INSTRUMENTATION

This application claims priority to U.S. Ser. No. 11/756,168, entitled SPINE SURGERY METHOD AND INSTRUMENTATION, filed May 31, 2007 now U.S. Pat. No. 8,070,754, which is incorporated herein by reference.

I. BACKGROUND OF THE INVENTION

A. Field of Invention

This invention pertains to the art of methods and apparatuses regarding spine surgery and more specifically relates to surgical procedures and associated instrumentation used to position an implant within an intradiscal space between two adjacent vertebral bodies.

B. Description of the Related Art

The volume of spinal surgeries to treat degenerative disc and facet disease has steadily increased over the past decade, fueled by population demographics and advancements in diagnostic and instrumentation adjuncts. Improvements in intraoperative radiological imaging and surgical technique have generated a great deal of interest in applying minimally invasive surgical (MIS) techniques to spinal applications. As in other surgical subspecialties, it is hoped such minimally invasive techniques applied to spinal surgery will result in less soft tissue trauma, less operative blood loss, reduced operative time, faster recovery periods and lower costs.

Known spinal surgical techniques, though generally working well for their intended purposes, have been adopted from traditional open surgical (non-MIS) techniques. As a result, known spinal surgical methods, instrumentation and interbody implants have limitations. One limitation is that the physical components are relatively large and bulky. This reduces surgeon visualization of the surgical site. Another limitation of known spinal surgical methods is that known surgical tools and implants are cumbersome and difficult to maneuver within the limited surgical space available. The limitations of current instrumentation in MIS spine surgery are noted particularly with regards to interbody fusion surgery.

The present invention provides methods and apparatuses for overcoming these limitations by providing surgical instrumentation that allows for minimally invasive spinal surgery and that provides for precise movement and placement of an implant into the disc space. The inventive instrumentation provides centralized distraction of the disc space, assuring optimized interspace sizing and annular distraction, without inhibiting the placement of interbody fusion devices.

II. SUMMARY OF THE INVENTION

According to one embodiment of this invention, a method of placing an implant into a disc space between a pair of spinal vertebrae, comprises the steps of: (a) providing a distractor and an inserter having a distractor/inserter rail/groove interconnection; (b) placing a distal end of the distractor into the disc space between the pair of spinal vertebrae; (c) placing the implant at a proximal end of the distractor; (d) placing the inserter into the distractor/inserter rail/groove interconnection and against the implant; (e) moving the inserter along the distractor/inserter rail/groove interconnection to thereby move the implant from the proximal end of the distractor to the distal end of the distractor; and, (f) inserting the implant into the disc space.

According to another embodiment of this invention, the step of moving the inserter along the distractor/inserter rail/groove interconnection, comprises the step of: moving the implant along a distractor/implant rail/groove interconnection.

According to another embodiment of this invention, the step of moving the inserter into the distractor/inserter rail/groove interconnection and against the implant, comprises the step of: placing the inserter into an inserter/implant concave/convex interconnection.

According to still another embodiment of this invention, the step of moving the comprises the step of: tightening the concave surface against the convex surface.

According to yet another embodiment of this invention, the step of moving the inserter along the distractor/inserter rail/groove interconnection, comprises the steps of: (a) moving the inserter and implant along a substantially linear path; and, (b) moving the inserter and implant along a curved path.

According to another embodiment of this invention, the method also comprises the steps of: (a) providing a cable that is operatively connected to the implant; (b) attaching the cable to the inserter; and, (c) applying tension to the cable with a cable tensioning device attached to the inserter.

According to another embodiment of this invention, surgical instrumentation for use in placing an implant into a disc space between a pair of spinal vertebrae comprises: (a) a distractor having a distal end that may be placed into the disc space between the pair of spinal vertebrae; (b) an inserter for use in moving the implant toward the disc space between the pair of spinal vertebrae; and, (c) a distractor/inserter rail/groove interconnection that interconnects the distractor and the inserter for relative movement thereby.

According to another embodiment of this invention, the distractor/inserter rail/groove interconnection comprises: (a) at least one rail formed on the distractor; and, (b) at least one groove formed in the inserter that receives the rail.

According to another embodiment of this invention, the distractor/inserter rail/groove interconnection comprises: (a) at least one rail formed on the inserter: and, (b) at least one groove formed in the distractor that receives the rail.

According to still another embodiment of this invention, the distractor/inserter rail/groove interconnection can be disconnected by application of a nominal force perpendicular to the direction of the rail length.

According to yet another embodiment of this invention, the distractor/inserter rail/groove interconnection cannot be disconnected by application of a nominal force perpendicular to the direction of the rail length.

According to another embodiment of this invention, the distal end of the distractor comprises a curvilinear shape along the length of the distractor and the proximal end of the distractor comprises a substantially linear shape along the length of the distractor.

According to another embodiment of this invention, the surgical instrumentation further comprises an inserter/implant concave/convex interconnection.

According to another embodiment of this invention, the concave surface can be adjusted to tighten the connection to the convex surface.

According to another embodiment of this invention. the surgical instrumentation further comprises a distractor/implant rail/groove interconnection that interconnects the distractor and the implant for relative movement thereby.

According to still another embodiment of this invention, the surgical instrumentation further comprises a cable that is operatively connected to the implant and that extends at least partially through the inserter.

According to yet another embodiment of this invention, the surgical instrumentation further comprises a cable tensioning device whereby tension can be applied to the cable.

According to another embodiment of this invention, surgical instrumentation for use in placing an implant that is deployable by a cable into a disc space between a pair of spinal vertebrae comprises: (a) a distractor having a first portion that may be placed into the disc space between the pair of spinal vertebrae; and (b) an inserter, including a cable tensioning device, for use in moving the implant into the disc space between the pair of spinal vertebrae.

One advantage of this invention is that the inventive surgical instrumentation permits an implant to be relatively easily placed into a disc space between a pair of spinal vertebrae.

Another advantage of this invention is that the implant may be relatively easily and securely attached to the inserter and then detached from the inserter.

Still another advantage of this invention is that the distractor and inserter may easily move relative to each other along a distractor/inserter rail/groove interconnection to insert the implant.

Another advantage of this invention is that the surgeon may make consistent and reproducible biplanar, midline placement of the interbody implant.

Another advantage of this invention, according to one embodiment, is that the surgeon may easily make adjustments in positioning the interbody implant because of the centralized placement of the distractor and its possible motion with the inserter and interbody implant as a single moveable unit until surgeon preference dictates disengagement.

Another advantage of this invention is that the surgical instrumentation allows for minimally invasive deployment via either an anterior, anterolateral, posterior or posterolateral approach, with the latter approach possible via either a transforaminal or extraforaminal approach.

Yet another advantage of this invention, according to one embodiment, is that the centralized distraction instrument is functionally integrated with the implant and the inserter. This permits measured and controlled placement of the interbody implant.

Still other benefits and advantages of the invention will become apparent to those skilled in the art to which it pertains upon a reading and understanding of the following detailed specification.

III. BRIEF DESCRIPTION OF THE DRAWINGS

The invention may take physical form in certain parts and arrangement of parts, embodiments of which will be described in detail in this specification and illustrated in the accompanying drawings which form a part hereof and wherein.

IV. DETAILED DESCRIPTION OF INVENTION

Figure 1:
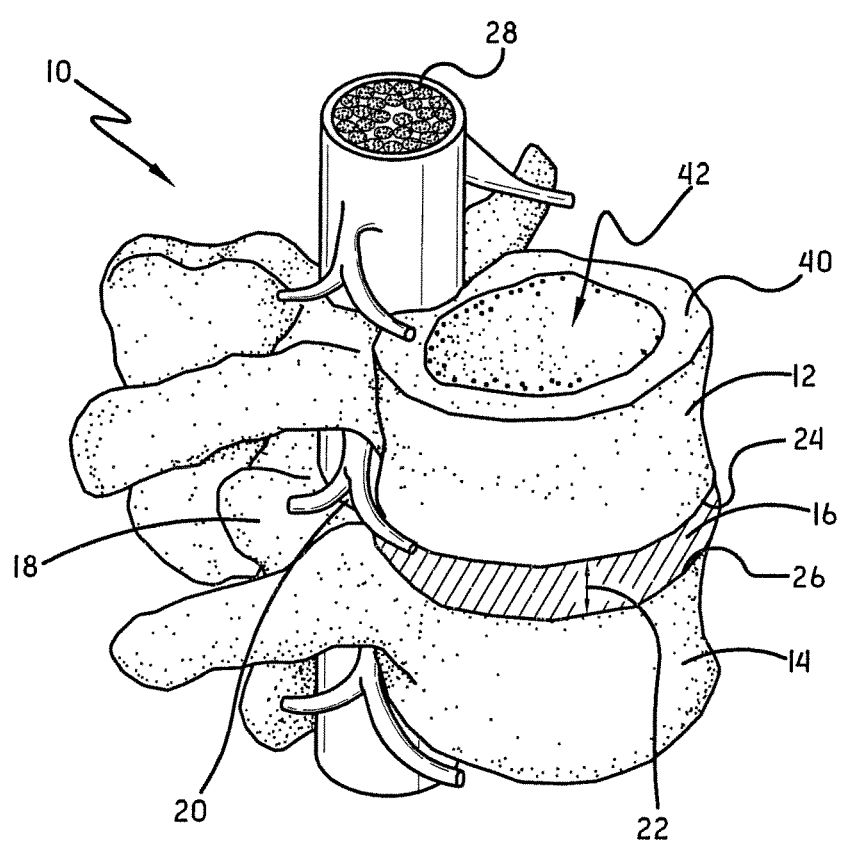
FIG. 1 is a side perspective view of a spinal segment.
Figure 2:
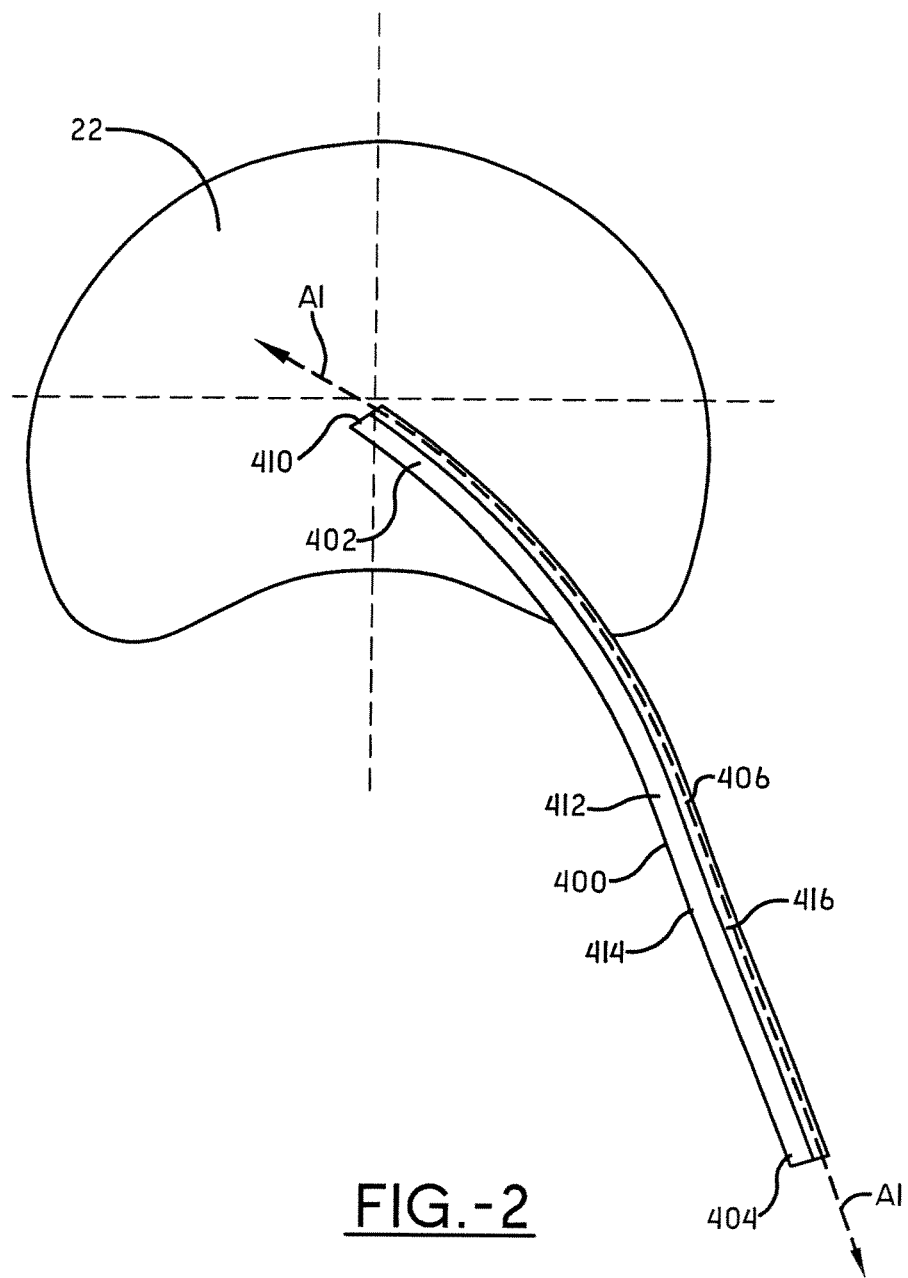
FIG. 2 is an illustrative top view of a distractor according to one embodiment of this invention positioned in an intradiscal space.
Figure 3:
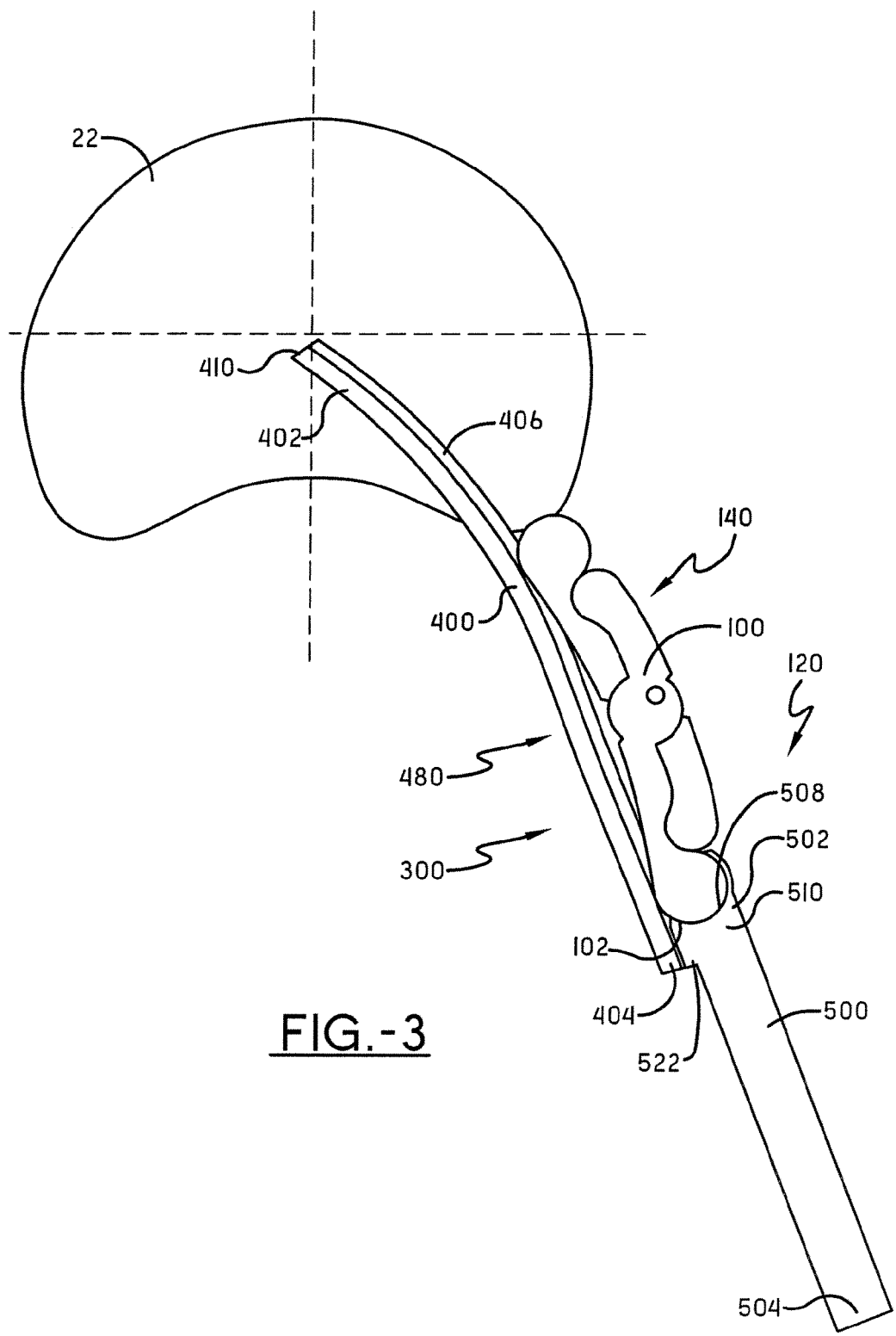
FIG. 3 is an illustrative top view as in FIG. 2 but also showing an inserter and an implant according to certain embodiments positioned at a proximal end of the distractor.
Figure 4:
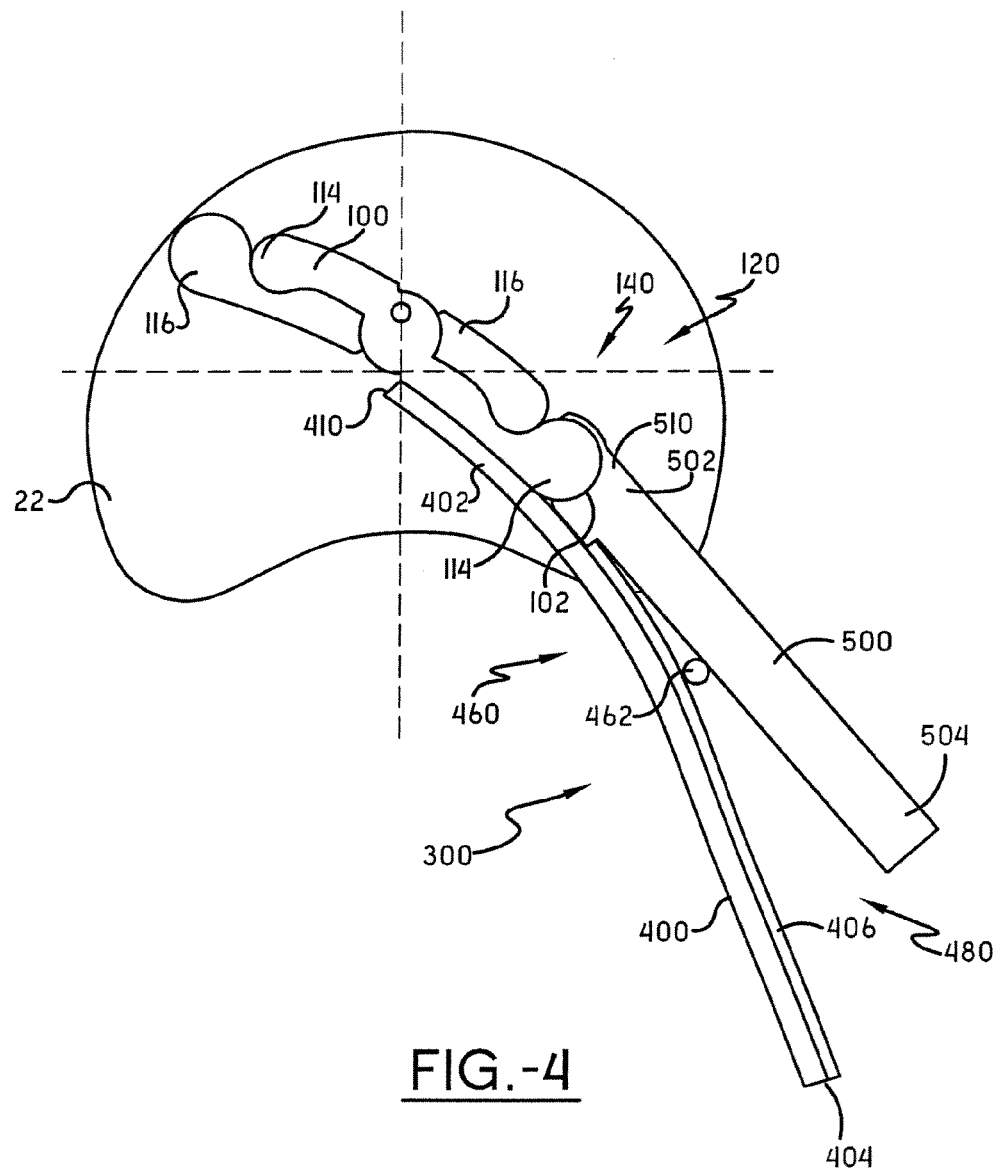
FIG. 4 is an illustrative top view as in FIG. 3 but showing the inserter and implant moved to the distal end of the distractor.
Figure 5:
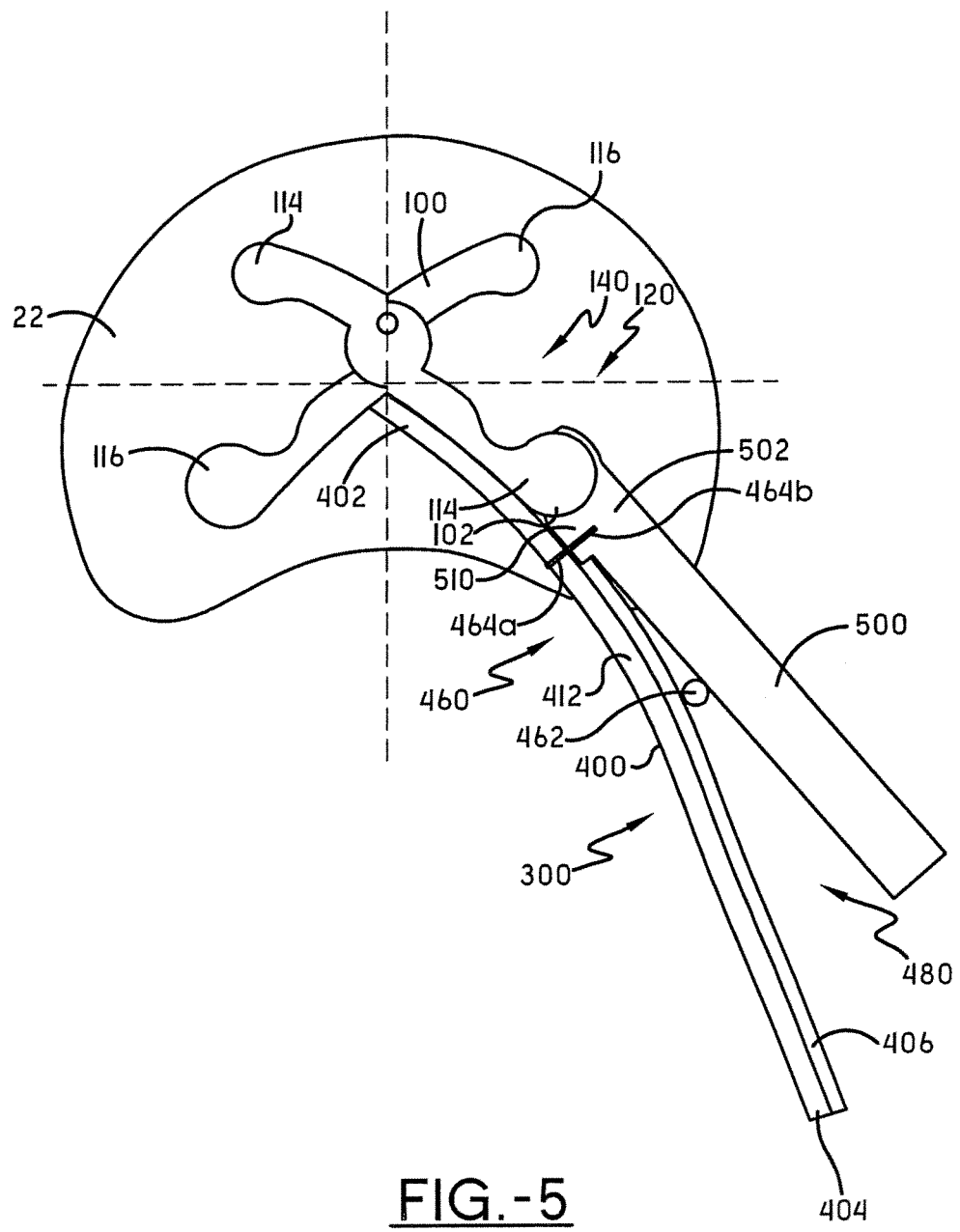
FIG. 5 is an illustrative top view as in FIG. 4 but showing the implant in a deployed state.
Figure 6:
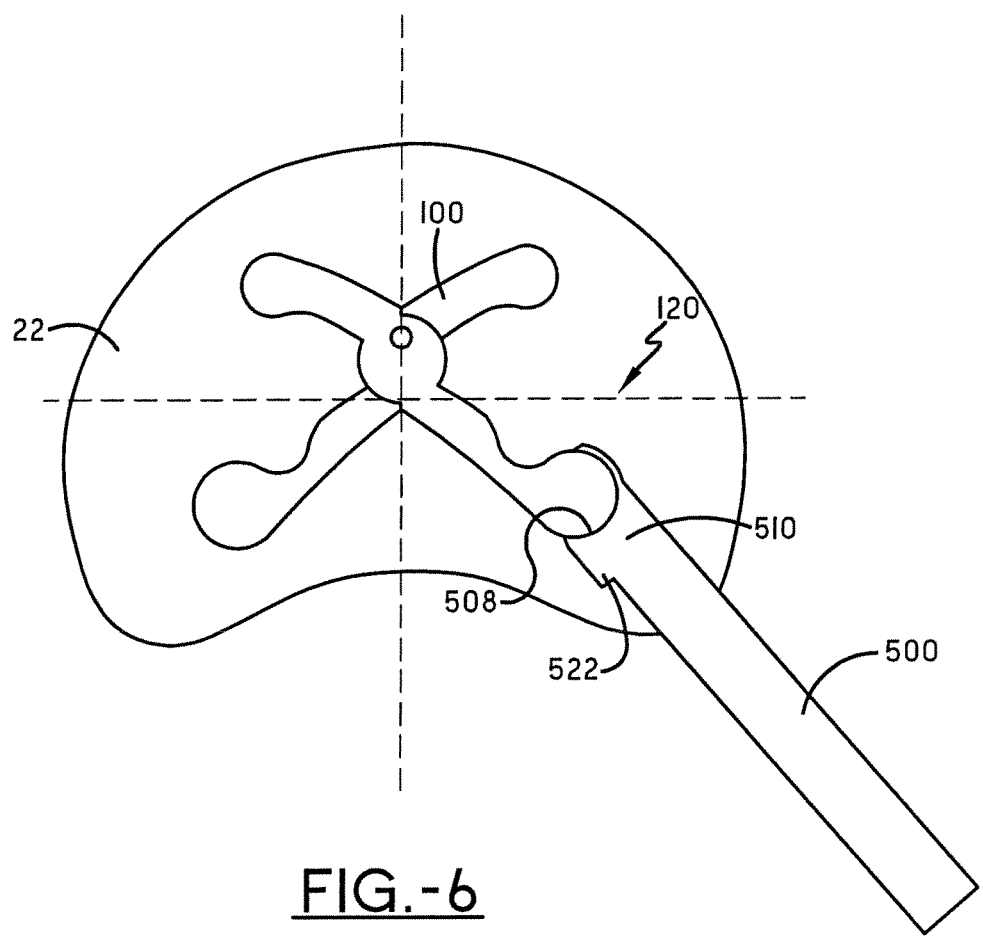
FIG. 6 is an illustrative top view as in FIG. 5 but showing the distractor removed.
Figure 7:
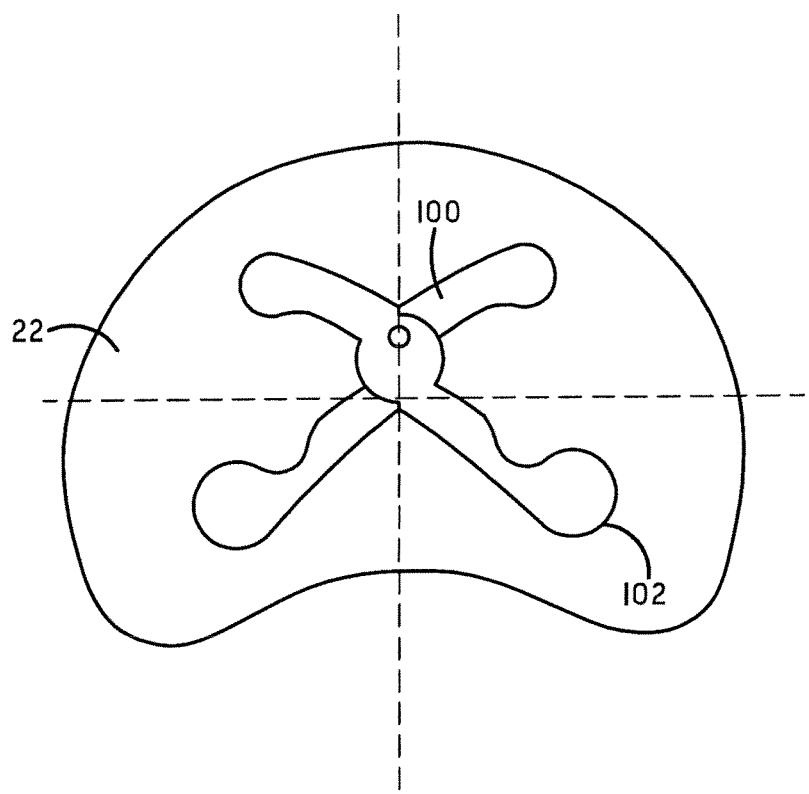
FIG. 7 is an illustrative top view as in FIG. 6 but showing the inserter removed.
Figure 8:
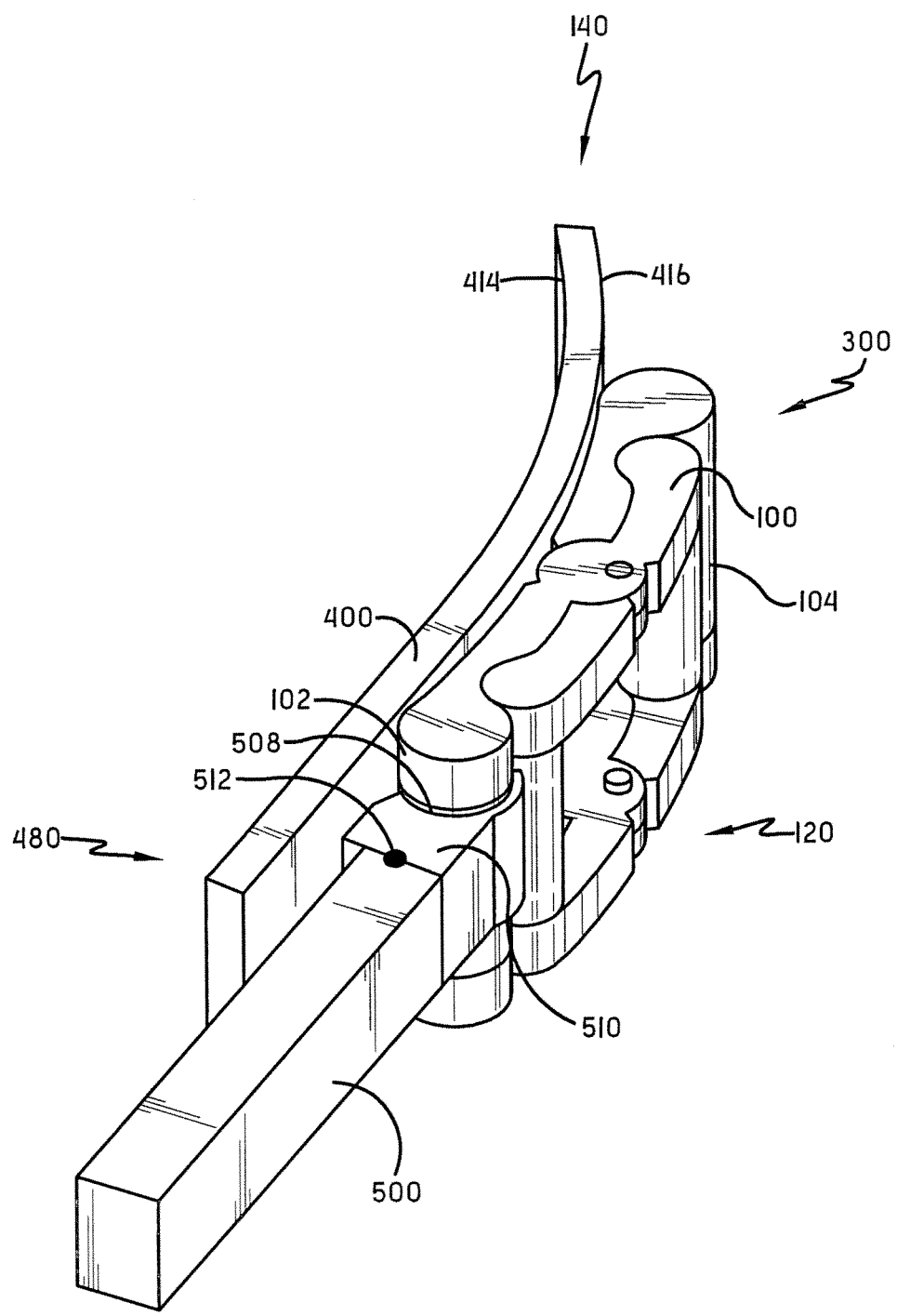
FIG. 8 is a perspective view of an inserter and implant according to certain embodiments positioned on a distractor.

Referring now to the drawings wherein the showings are for purposes of illustrating embodiments of the invention only and not for purposes of limiting the same, FIG. 1 shows a portion of a spinal column, a spinal segment 10 that may use the surgical instrumentation 300 of this invention to insert an implant 100, as illustrated in FIGS. 2-5. The particular implant can be any implant chosen with sound engineering judgment. The implant 100 may be, for non-limiting examples, any of the implants described in commonly owned U.S. patent application Ser. No. 11/236,068, publication number US 2007/0073398 A1, published on Mar. 29, 2007, titled SPINE SURGERY METHOD AND IMPLANT. which is incorporated herein by reference. The spinal segment 10 is made up of two vertebrae 12, 14 attached together by ligaments with a disc 16 separating them. Facet joints 18 fit between the two vertebrae 12, 14 and allow for movement. The neural foramen 20 between the vertebrae 12, 14 allow space for the nerve roots to travel freely from the spinal cord 28 to the body. The disc 16 occupies the intradiscal space 22. By intradiscal space 22 it is meant the space usually occupied by the disc 16 between two adjacent vertebral bodies 12, 14 and more specifically the space 22 between adjacent endplates 24, 26 of the vertebral bodies 12, 14 as shown. As the components and operation of a spinal column is well known to those of skill in the art, further detail will not be provided here.

With reference now to FIGS. 2-7 the surgical instrumentation 300 is illustrated being used to insert the implant 100 within the intradiscal space 22. The surgical instrumentation 300 may include a distractor 400 having a distal end 402 that may be placed into the disc space 22 and an inserter 500 for use in moving the implant 100 toward the disc space 22. The distractor 400 may be functionally integrated with the inserter 500 to simplify the required surgical technique and to make it easy to match the inserter 500 with the distractor 400 to be used. The functional integration may be achieved with the use of a distractor/inserter rail/groove interconnection 480 that interconnects the distractor 400 and the inserter 500 and permits relative motion of the distractor 400 with respect to the inserter 500. The expression "rail/groove interconnection" means a connection between at least two components where at least one of he components has at least one rail and at least another component has at least one groove or channel that receives the rail and that permits the two components to move relative to each other along the rail/groove connection. The expression "distractor/inserter rail/groove interconnection" means a rail/groove interconnection where the two components are the distractor 400 and the inserter 500. In one embodiment, illustrated in FIGS. 8-12, the distractor/inserter rail/groove interconnection 480 comprises at least one rail 406 formed on the distractor 400 and at least one groove 506 formed in the inserter 500. In another embodiment, not shown, the distractor/inserter rail/groove interconnection 480 comprises at least one rail formed on the inserter 500 and at least one groove formed in the distractor 400.

Figure 17:
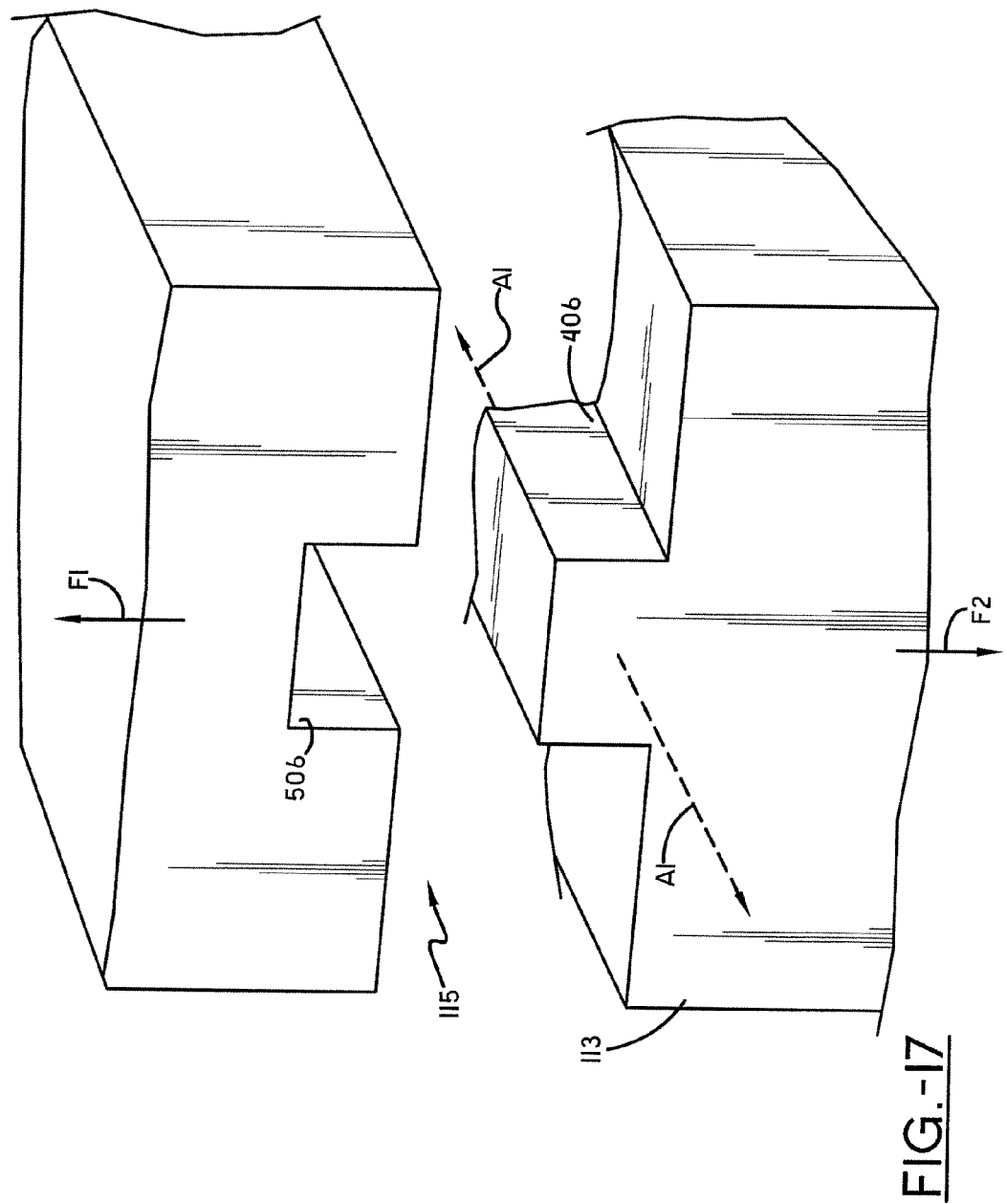
FIG. 17 illustrates one embodiment of a rail/groove interconnection, shown disconnected, that may be disconnected by application of a nominal force perpendicular to the longitudinal axis of the rail.

With reference now to FIGS. 1-5 and 8-12 the particular design of the rail 406 and groove 506 can be any chosen with sound engineering judgment. In one embodiment, it may be desirable for the surgeon to be able to remove the inserter 500 from the distractor 400 without relative movement along the rail 406. To accomplish this, the distractor/inserter rail/groove interconnection 480 may be disconnected by application of a force perpendicular o the longitudinal axis of the rail. This is illustrated in FIG. 17 which show a rail/groove interconnection 115 comprising a first component 111 (which for a distractor/inserter rail/groove interconnection could be either the distractor 400 or the inserter 500) and a second component 113 (which for a distractor/inserter rail/groove interconnection could be either the inserter 500 or the distractor 400). The first component 111 has a groove 506 that receives a rail 406 in the second component 113. The rail 406 may have a longitudinal axis A1. Because there is sufficient clearance between the outer walls of the rail 406 and the inner walls of the groove 506, after connection the rail/groove interconnection 115 may be disconnected by application of a force perpendicular to the longitudinal axis A1 of the rail 406. This force may be a first force F1 applied as shown to the first component 111, a second force F2 applied as shown to the second component 113, or a combination of the application of the first and second forces F1, F2. As can be readily understood by those of skill in the art, there are multiple rail and groove shapes that would permit disconnection of the rail/groove interconnection by application of a force perpendicular to the longitudinal axis of the rail. In a more specific embodiment, the rail/groove interconnection 115 may be designed to require a certain minimum force to be applied before the rail/groove interconnection 115 disconnects. Thus, for example, the rail/groove interconnection 115 may be designed such that a force only equal to the weight of the components (such as when the surgeon is not contacting the components) is insufficient to disconnect the interconnection but when the surgeon applies a predetermined force the rail/groove interconnection 115 disconnects. This would have the advantage of preventing the possibility of the first component 111 from "slipping off" or "falling off" the second component 113 inadvertently.

Figure 18:
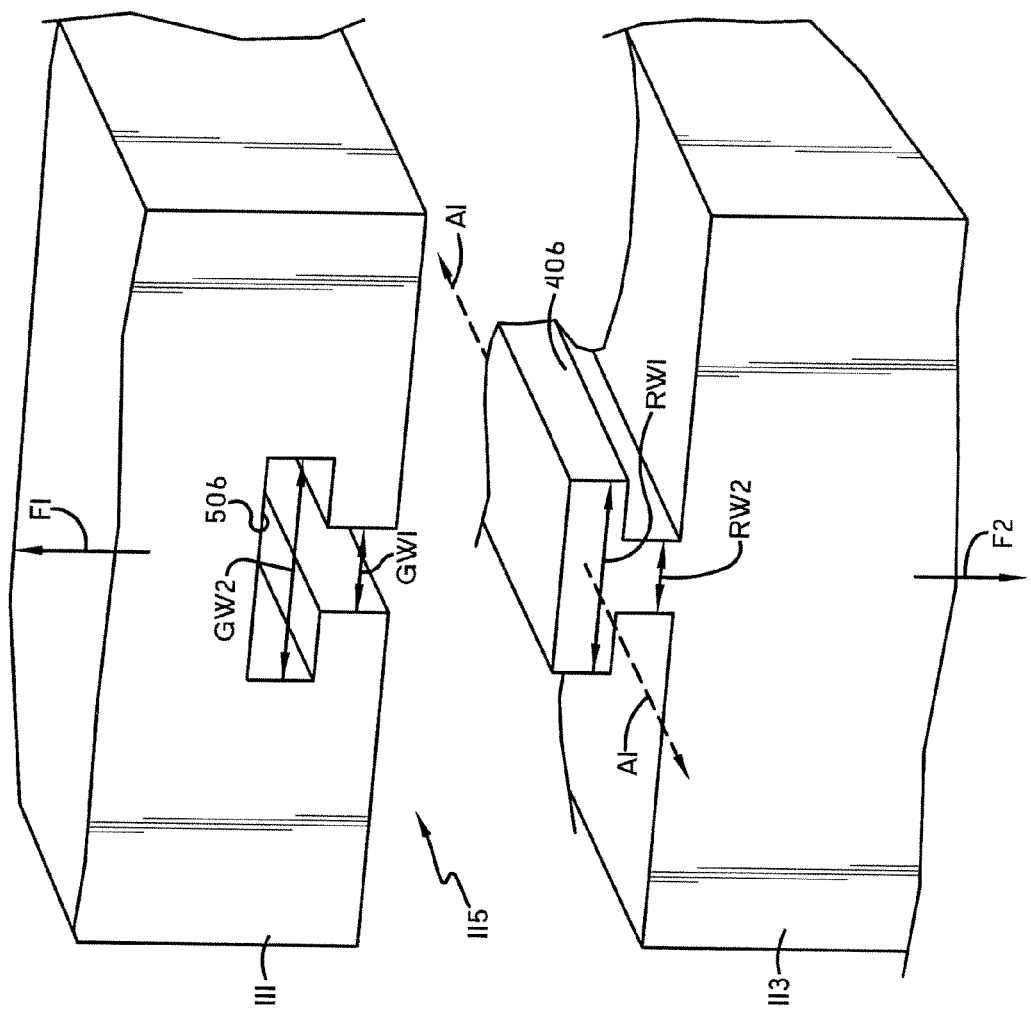
FIG. 18 illustrates one embodiment of a rail/groove interconnection, shown disconnected, that may not be disconnected by application of a nominal force perpendicular to the longitudinal axis of the rail.

With continuing reference to FIGS. 1-5 and 8-12, in another embodiment, it may be desirable to prevent the removal of the inserter 500 from the distractor 400 except by relative movement along the rail 406. This would have the advantages of: (a) preventing the possibility of the first component from "slipping off" or "falling off" the second component inadvertently; (b) preventing the possibility of the first component from being "bumped off" the second component inadvertently by the surgeon; and, (c) making a stronger rail/groove interconnection. To accomplish this, the distractor/inserter rail/groove interconnection may not be disconnected by application of a nominal force perpendicular to the longitudinal axis of the rail. By "nominal force" it is meant a force that is typically to be incurred in surgery including the weight of the components and the forces the surgeon may apply. This is illustrated in FIG. 18 which shows a rail/groove interconnection 115 comprising a first component 111 (which for a distractor/inserter rail/groove interconnection could be either the distractor 400 or the inserter 500) and a second component 113 (which for a distractor/inserter rail/groove interconnection could be either the inserter 500 or the distractor 400). The first component 111 has a groove 506 that receives a rail 406 in the second component 113. The rail 406 has a longitudinal axis A1. Because there is insufficient clearance between the outer walls of the rail 406 and the inner walls of the groove 506, after connection the rail/groove interconnection 115 may not be disconnected by application of a nominal force (such as force F1 and/or F2) perpendicular to the longitudinal axis A1 of the rail 406. As can be readily understood by those of skill in the art, there are multiple rail and groove shapes that would not permit disconnection of the rail/groove interconnection by application of a nominal force perpendicular to the longitudinal axis of the rail. In one embodiment, shown, this is accomplished with the use of a groove 506 having at least a first relatively outer width GW1 and a second relatively inner width GW2 that is substantially greater than the first relatively outer width GW1 and a rail 406 having a at least a first relatively outer width RW1 and a second relatively inner width RW2 that is substantially smaller than the first relatively outer width RW1. In a more specific embodiment, shown in FIGS. 9, 10 and 12 both the rail 406 and groove 506 have a tapered shape.

With reference now to FIGS. 1-5 and 10, the distractor 400 may have a distal end 402 and a proximal end 404. The distal end 402 may be placed between the endplates 24, 26 of the vertebral bodies 12, 14 to distract the disc space 22. The distal end 402, in one embodiment, has a curvilinear shape along the length of the distractor 400, as shown. The curvilinear shape may have, in one embodiment, a constant radius of curvature or, in another embodiment, a variable radius of curvature. The particular extent of curvature and the particular length of the distractor 400 that encompasses the curvilinear shape may be varied. The length of the distractor 400 that encompasses the curvilinear shape may be long enough to allow full advancement into the disc space 22; a space that typically will range from about 5 (millimeters) mm to 50 mm. This range is illustrative only and should not limit this invention in any way. In one embodiment, the particular curvilinear shape of the distractor 400 is selected by the surgeon to match the spinal anatomy of the patient being operated on. In a more specific embodiment, the curvilinearity of the distractor 400 may be selected to match the initial curvilinearity of the guidewires (not shown) placed in the center of the disc space 22. Variable degrees of curvature are offered in these guidewires, preliminarily chosen on the basis of templating of the corresponding disc space 22 on axial cut CT or MRI images. The best fit to reach the center of the disc space 22 in the anteroposterior and lateral planes is selected based on the surgeon's choice of approach. As a non-limiting example, the degree of curvilinearity may be greater for a posterolateral approach versus an extraforaminal approach. The degree of curvilinearity of the guidewire and hence, the distractor 400, may be dictated by the distance from the center of the disc space 22 to the annulus, that is, the entry point of the implant 100 into the disc space 22. This may be variable, but for example, in the posterolateral approach, the angle from the center of the disc space 22 to the annular entry point may be approximately 34 degrees off the Y-axis, where the Y-axis is defined as the sagittal axis of the disc space 22. The guidewire and distractor 400 for a tranforaminal, or extraforaminal approach, however, may be approximately 45 degrees off the Y-axis.

Figure 9:
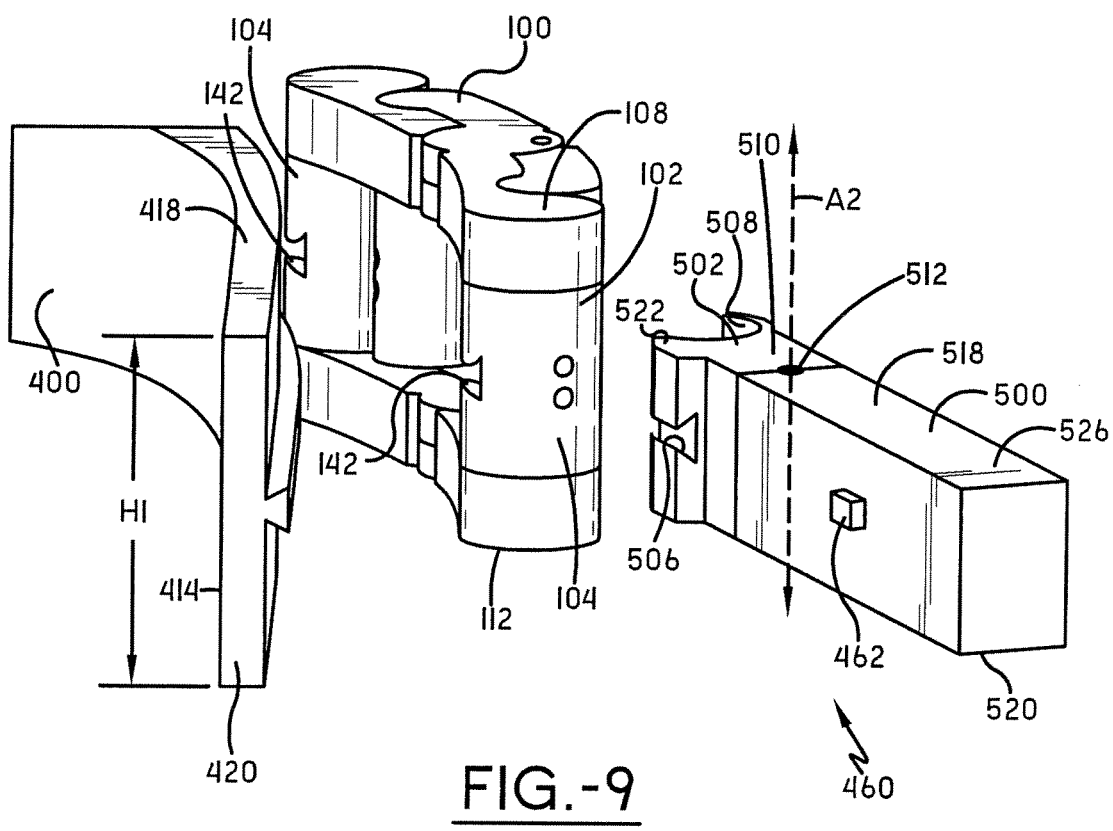
FIG. 9 is a perspective view of the distractor, inserter, and implant of FIG. 8 but in a disengaged condition.
Figure 10:
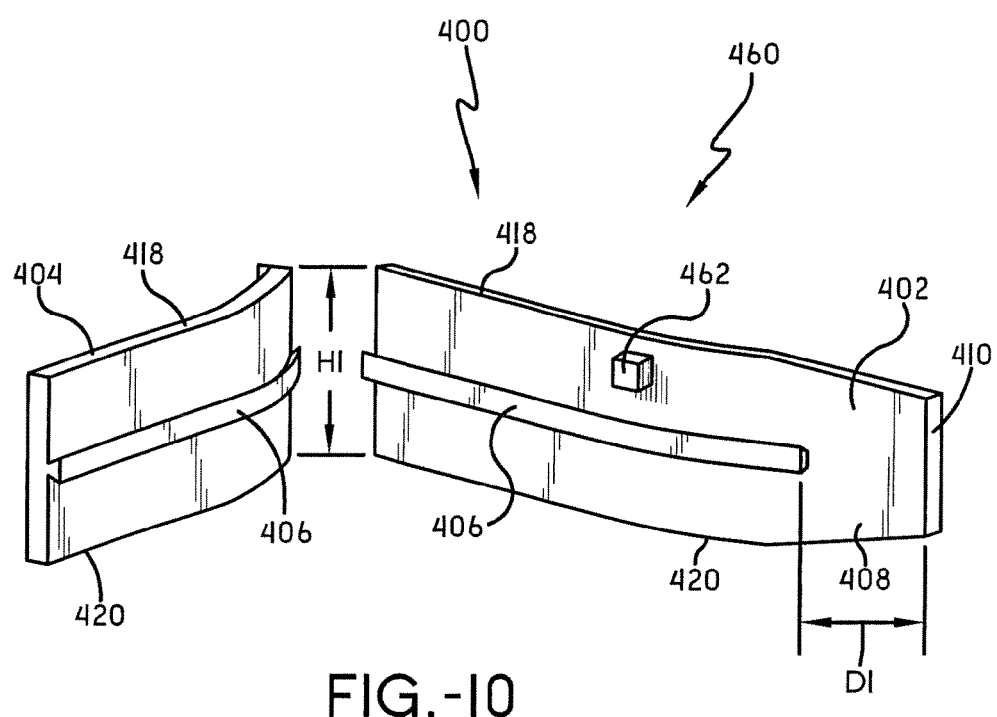
FIG. 10 is a perspective view of portions of a distractor.

With reference now to FIGS. 2-5 and 9-10, in one embodiment, the proximal end 404 of the distractor 400 has a substantially linear shape along the length of the distractor 400, as shown. The distractor 400 may have a height H1 (FIGS. 9-10) that varies along the length of the distractor 400 up to 20 millimeters (mm). This range is illustrative only and should not limit this invention in any way. In one embodiment, the distal end 402 of the distractor 400 comprises a tapered blade 408 (FIG. 10). The degree of taper may vary, depending on need. In one embodiment, the blade tapers down to a tip 410 (FIG. 10). For one typical non-limiting example, the tip 410 may be 5 mm tapering to a full or maximum height H1 of 15 mm. In one embodiment, the junction point of the proximal end 404 and the distal end 402 is also the junction point 412 (FIGS. 1 and 5) of the curvilinear shape and the substantially straight portion. In another embodiment, the full height point of the distractor 400 is the junction point 412 of the curvilinear shape and the substantially straight portion with the height H1 tapering down to the tip 410.

With continuing reference to FIGS. 2-5 and 9-10 and 13, in one embodiment, the distractor 400 may have a pair of sides 414, 416 and a pair of edges 418, 420. The distractor 400 may also have a rail 406 that extends from one of the sides 414, 416. In other embodiments, multiple rails may be used. The rail 406 shown is positioned equidistant from the edges 418, 420 of the distractor 400. In other embodiments, the rail or rails may be asymmetrically located. For the embodiment shown, the rail 406 extends from the convex side 416 of the distractor 400 but it should be understood that in another embodiment the rail 406 may extend from the concave side 414 of the distractor 400. In one embodiment shown, the rail 406 extends the entire length of the distractor 400. In another embodiment, the rail 406 does not extend the entire length of the distractor 400. One example is shown in FIG. 10 where it can be seen that the rail 406 ends before the distal end 402 of the distractor 400. The distance D1 between the end of the rail 406 and the tip 410 may be determined based on the particular inserter 500 and/or particular implant 100 that is used to properly place the implant 100 within the disc space 22. In one embodiment, the distance D1 is proportionate to the length of the implant 100 being inserted. In this case, the distance D1 would be correspondingly greater for an implant 100 having a greater length along longitudinal axis. A distractor handle 440 that the surgeon may hold to manipulate the distractor during surgery may be attached to the proximal end 404. In one embodiment, each distractor 400 size has a corresponding dedicated distractor handle 440 that fits the distractor's height H1, width W1, and curvature (if any). In another embodiment, the distractor handle 440 can be adjusted to fit various distractor 400 sizes.

Figure 12:
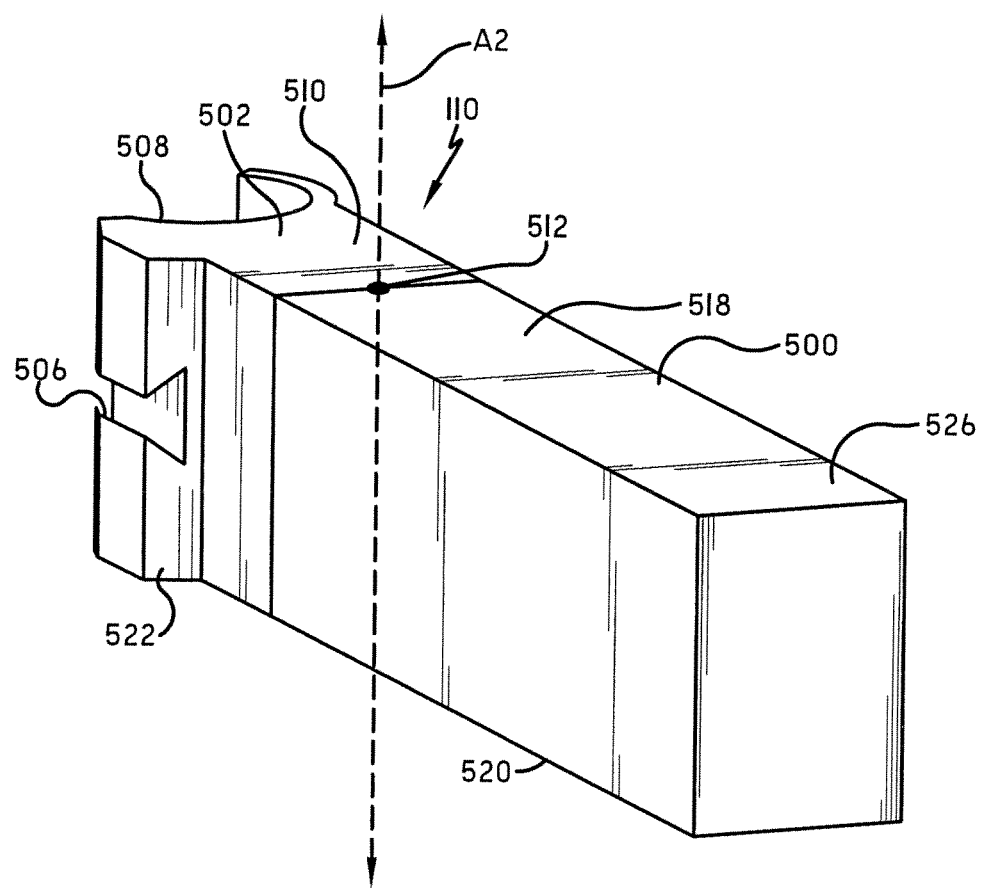
FIG. 12 is a perspective view of the inserter shown in FIG. 9.
Figure 13:
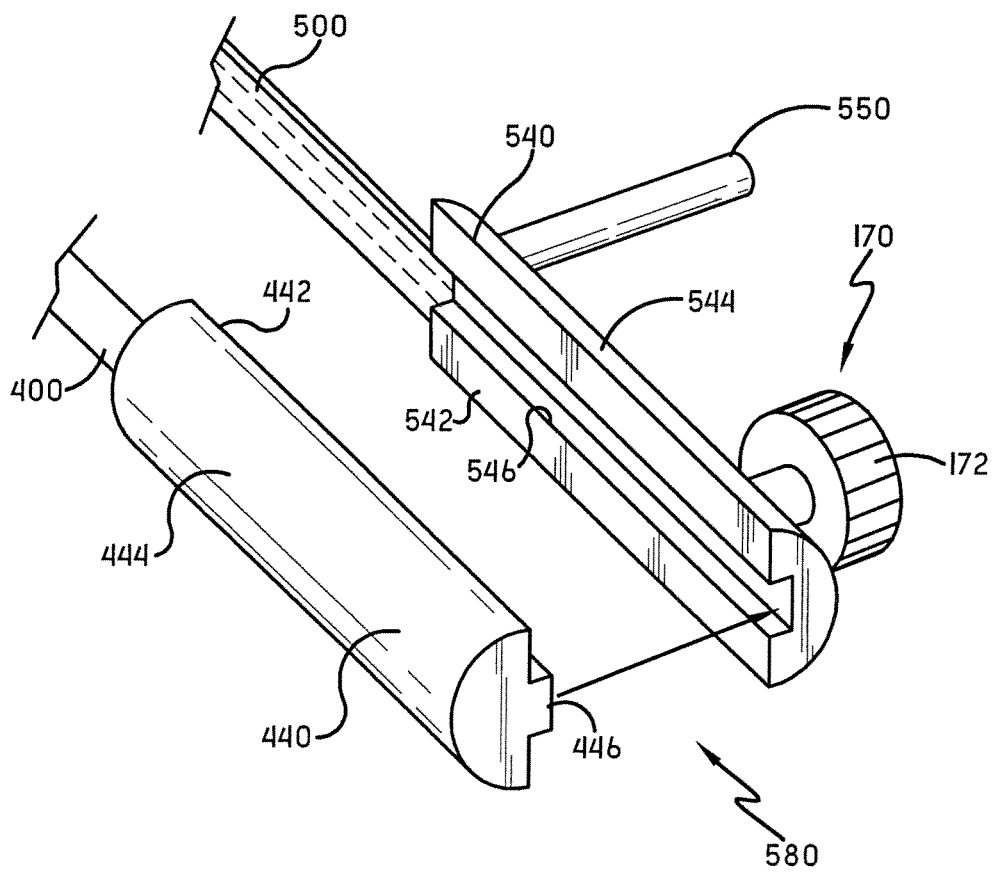
FIG. 13 is a perspective view of a portion of a distractor and inserter according to an embodiment of this invention.
Figure 14:
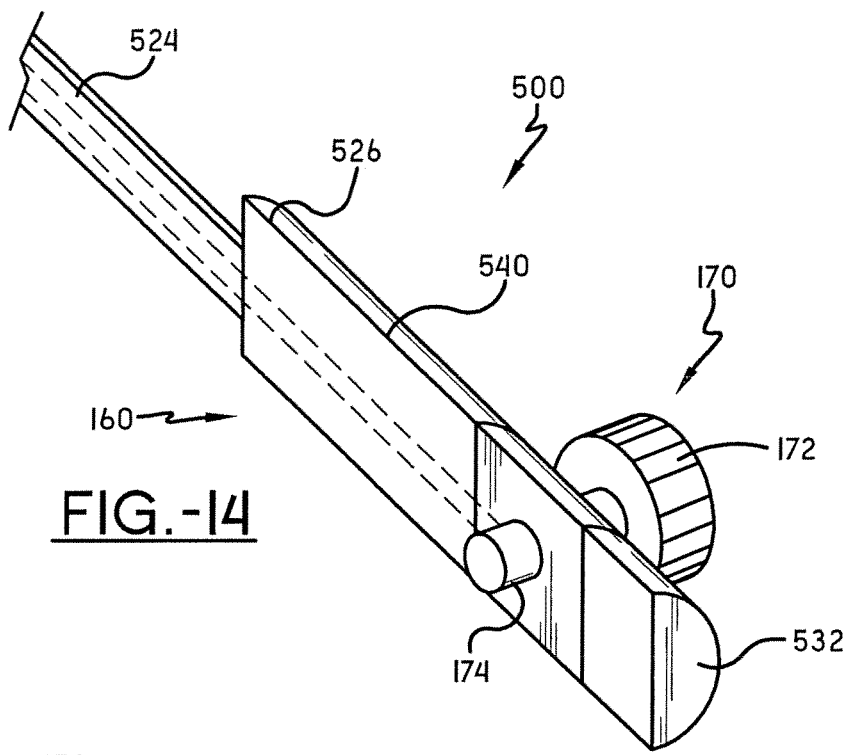
FIG. 14 is a perspective view of a portion of an inserter according to an embodiment of this invention.
Figure 15:
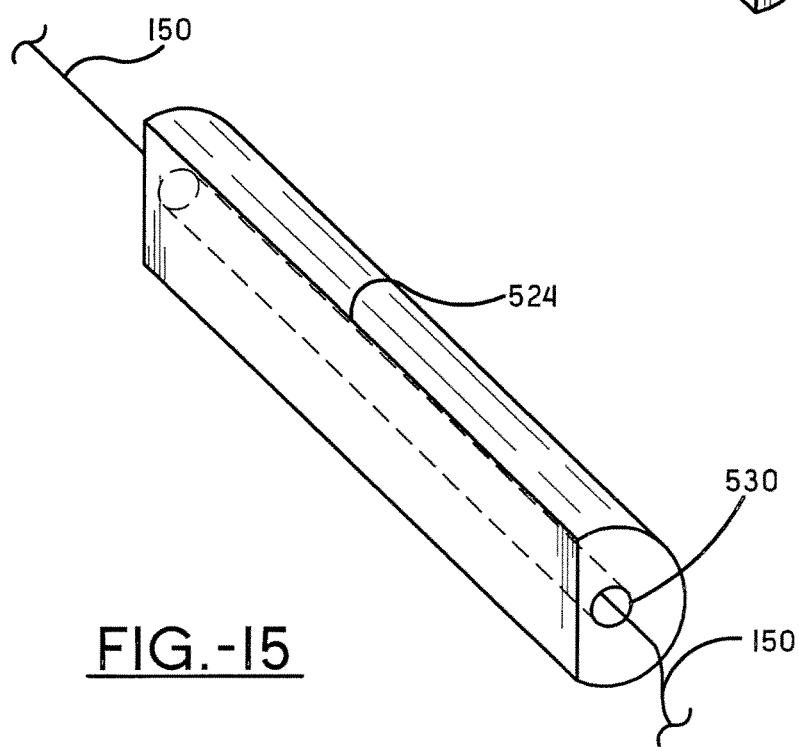
FIG. 15 is a perspective view of a portion of the inserter body member shown in FIG. 14.
Figure 16:
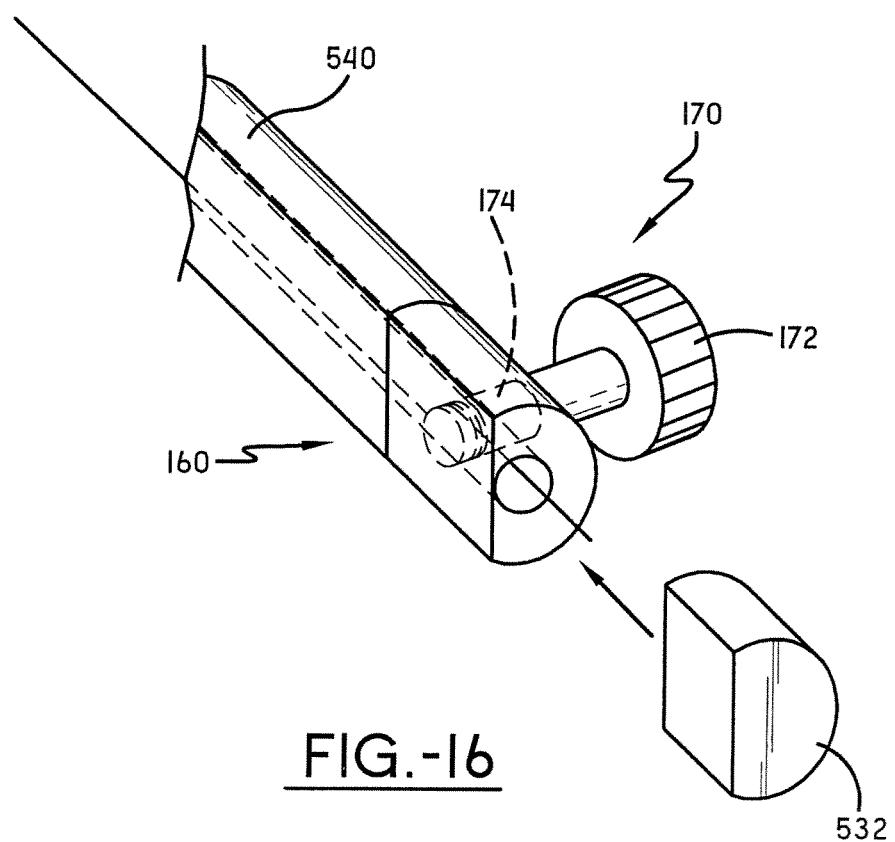
FIG. 16 is an assembly view of a cap that may be attached to the inserter handle of FIG. 14.

With reference now to FIGS. 3-6, 8-9, and 12, in one embodiment the inserter 500 may have a groove 506 that receives the rail 406. In other embodiments, multiple grooves may be used. The groove 506 shown is positioned equidistant from the edges 518, 520 of the inserter 500. In other embodiments, the groove or grooves may be asymmetrically located. In one embodiment, the groove 506 extends the entire length of the inserter 500. In another embodiment, the groove 506 does not extend the entire length of the inserter 500. One example is shown in FIGS. 9 and 12 where it can be seen that the groove 506 is formed at a distal end 502 of the inserter 500 in a lip portion 522. The distal end 502 may include a contact surface 508 which is used to contact the implant 100 to move the implant 100 toward the disc space 22. The contact surface 508 may be part of an end section 510 that may pivot with respect to the inserter 500 about a hinge joint 512 having an axis A2 that is substantially parallel to a line that bisects the edges 518, 520 and that is substantially perpendicular to the longitudinal axis of the inserter 500. The hinge joint 512 may be positioned at any location along the longitudinal axis of the inserter 500 chosen with sound engineering judgment. The specific position for the hinge joint 512 may be determined based on: (a) the specific surgical approach selected by the surgeon (which determines the curvilinearity required); and, (2) the size of the implant 100 to be inserted. In another embodiment, the end section 510 does not pivot with respect to the inserter 500 but is fixed to the inserter 500 at a predetermined angle with respect to the inserter 500 that can range between 0 degrees to 180 degrees. As a non-limiting example, the posterolateral approach may have a curvilinearity of approximately 34 degrees off the previously described Y-axis. The corresponding predetermined fixed angle of the end section 510 with respect to the inserter 500 may correlate with that curvilinearity. In yet another embodiment, the end section 510 may be formed of one or more flexible materials. The inserter 500 may have, as shown, a substantially linear shape along the length of the inserter 500. In another embodiment, not shown, the inserter 500 has a curvilinear shape. This curvilinear shape may match the curvilinear shape of the distractor 400. In one embodiment, shown in FIGS. 12, 14 and 15, the inserter 500 comprises a body member 524 and an outer shell or housing 526. The end section 510 may be attached to the body member 524 in a manner described above.

With reference now to FIGS. 13-16, an inserter handle 540 that the surgeon may hold to manipulate the inserter 500 during surgery may be attached to the proximal end 504. The inserter handle 540 may be, in one embodiment, attached to the end of the body member 524, as shown. In yet another embodiment, the inserter handle 540 and the distractor handle 440 may be functionally integrated. Each handle 540, 440 may have, for example, a relatively flat inner surface 542, 442 that engage each other or are affixed to each other. The handles 540, 440 may have a hemi-cylindrical cross-section with outer surfaces 544, 444 designed to engage the surgeon's hands. In a more specific embodiment, the handles 540, 440 may have mirror image shapes with the hemi-cylindrical cross-sections permitting closer apposition of the handles 540, 440 during the implant insertion process. In this case, when compressed together, the handles 540, 440 resemble a typical cylindrical shaft handle. The handles 540, 440 may utilize, in one embodiment, a handle/handle rail/groove interconnection 580 comprising a first component (which could be either the distractor 400 or the inserter 500) and a second component (which could be either the inserter 500 or the distractor 400) where the first component has a groove 546 that receives a rail 446 in the second component. In another embodiment, the previously described distractor/inserter rail/groove interconnection 480 may be entirely or partially incorporated into the handles 540, 440. In yet another embodiment, the inserter 500 may have a counter rotation handle 550 (FIG.

13) used by the surgeon to prevent errant migration/rotation of the inserter 500. In one embodiment, the counter rotation handle 550 extends from the proximal end 504 of the inserter 500.

Figure 19:
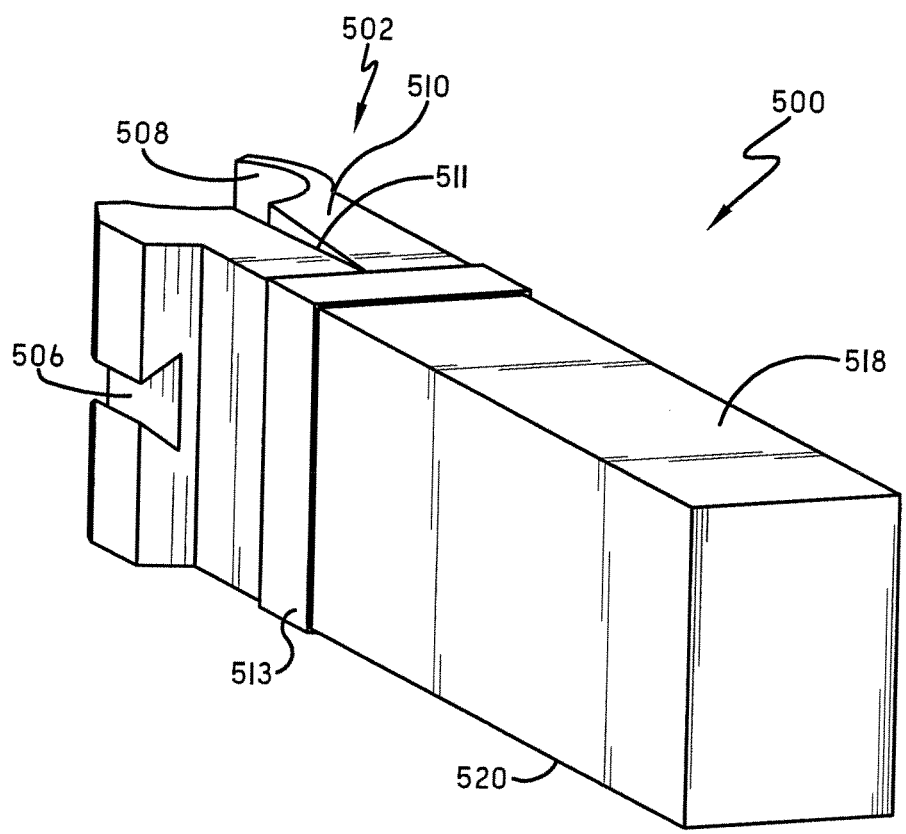
FIG. 19 is a perspective view of the inserter similar to that shown in FIG. 12 but illustrating an adjustment mechanism that can be used to tighten the connection of the concave surface to the convex surface.

With reference now to FIGS. 3-6, 8-9, and 11-12, in one embodiment, the inserter 500 is functionally integrated with the implant 100 to simplify the required surgical technique and to make it easy to match the inserter 500 with the implant 100 to be used. The functional integration may be achieved with the use of an inserter/implant concave/convex interconnection 120. The expression "concave/convex interconnection" means a connection between at least two components where at least one of the components has at least one concave surface and at least another component has at least one convex surface that receives the concave surface and that permits the two components to be moved together. The expression "inserter/implant concave/convex interconnection" means a concave/convex interconnection where the two components are the inserter 500 and the implant 100. In one embodiment, not shown, the inserter/implant concave/convex interconnection 120 comprises at least one concave surface formed on the implant 100 and at least one convex surface formed in the inserter 500. In another embodiment, shown in FIGS. 9 and 11-12, the inserter/implant concave/convex interconnection 120 comprises at least one convex surface 102 formed on the implant 100 and at least one concave surface, previously referenced contact surface 508 may be concave, formed in the inserter 500. In one specific example, the implant 100 may have one or more posts 104 that form the convex surface 102 received by the concave surface 508 formed in the inserter 500. In yet another embodiment, the inserter 500 may have an adjustment mechanism 110 of any type chosen with sound engineering judgment that can be used to tighten the connection of the concave surface 508 to the convex surface 102. In one specific embodiment, shown in FIG. 19 the inserter 500 has a slot 511 extending from one edge 518 to the opposite edge 520 along the longitudinal axis. The width of the inserter 500 may be reverse tapered so that it is wider at the distal end 502 towards the convex surface 508. A sleeve 513 is advanced down the length of the inserter 500 until it abuts the end section 510. Since the inserter 500 is wider at this end, advancing the sleeve 513 will compress the slot 511 thereby compressing the distal end 502 and tightening the fixation of the inserter 500 on the implant 100.

With reference now to FIGS. 3-5, 8-9 and 11, in one embodiment, the distractor 400 is functionally integrated with the implant 100 to simplify the required surgical technique and to make it easy to match the distractor 400 with the implant 100 to be used. The functional integration may be achieved with the use of a distractor/implant rail/groove interconnection 140 that interconnects the distractor 400 and the implant 100 and permits relative motion of the distractor 400 with respect to the implant 100. The expression "rail/groove interconnection", as defined above, means a connection between at least two components where at least one of the components has at least one rail and at least another component has at least one groove or channel that receives the rail and that permits the two components to move relative to each other along the rail/groove connection. The expression "distractor/implant rail/groove interconnection", means a rail/groove interconnection where the two components are the distractor 400 and the implant 100. In one embodiment, shown, the distractor/implant rail/groove interconnection 140 comprises at least one rail 406 formed on the distractor 400 and at least one groove 142 formed in the implant 100. In another embodiment, not shown, the distractor/implant rail/ groove interconnection 140 comprises at least one rail formed on the implant 100 and at least one groove formed in the distractor 400.

Figure 11:
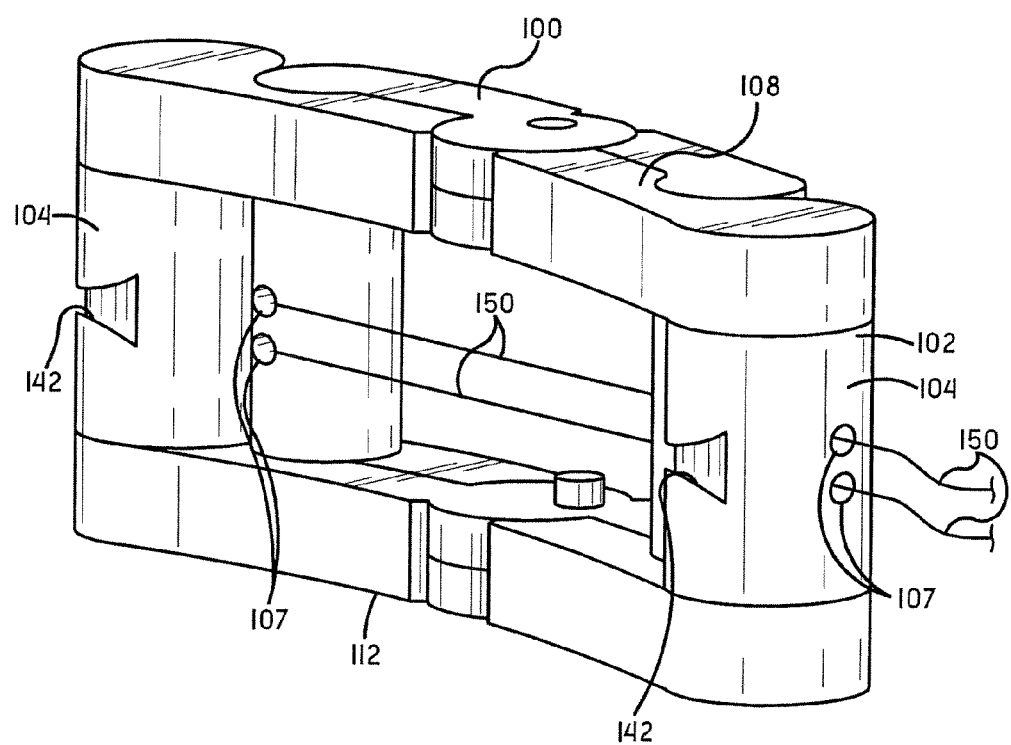
FIG. 11 is a perspective view of the implant shown in FIG. 9.

With reference now to FIGS. 9-11, in one embodiment, it may desirable for the surgeon to be able to remove the implant 100 from the distractor 400 without relative movement along the rail 406. To accomplish this, the distractor/implant rail/ groove interconnection 140 may be disconnected by application of a force perpendicular to the longitudinal axis of the rail 406. Designs similar to those discussed above regarding the rail/groove interconnection 115 may be used. In another embodiment, it may desirable to prevent the removal of the implant 100 from the distractor 400 except by relative movement along the rail 406. To accomplish this, the distractor/ implant rail/groove interconnection 140 may not be disconnected by application of a nominal force perpendicular to the longitudinal axis of the rail. Once again, designs similar to those discussed above regarding the rail/groove interconnection 115 may be used. In one embodiment, the implant 100 may have a single groove 142 that receives the rail 406. In other embodiments, multiple grooves may be used. Two such grooves 142, 142 are shown in FIGS. 9 and 11 where one groove 142 is provided in each post 104, 104. The grooves 142, 142 shown are positioned equidistant from the edges 108, 112 of the implant 100. In other embodiments, the groove or grooves may be asymmetrically located. In one embodiment, the groove 142 extends the entire length of the implant 100. In another embodiment, the groove 142 does not extend the entire length of the implant 100. In one embodiment, not shown, the implant 100 has a substantially linear shape along the length of the implant 100. In another embodiment, shown, the implant 100 has a curvilinear shape. This curvilinear shape may match the curvilinear shape of the distractor 400.

With continuing reference to FIGS. 2-5 and 9-10, in one embodiment a motion limiter 460 is provided to limit the relative movement of the distractor 400 and the inserter 500 along the distractor/inserter rail/groove interconnection 480. In one specific embodiment, shown in FIG. 10, the motion limiter 460 is in the form of an endstop 462 that is placed on the distractor 400. As the implant 100 affixed to the inserter 500 is moved along the distractor/inserter rail/groove interconnection 480, a portion of the inserter 500 (a part of the lip portion 522, for example) eventually contacts the endstop 462 preventing further advancement of the inserter 500 and thus preventing further advancement of the implant 100. The endstop 462 in this embodiment may be positioned so that the inserter 500 may contact it but the implant 100 does not. In another specific embodiment, shown in FIGS. 4 and 9, the motion limiter 460 is in the form of an endstop 462 that is placed on the inserter 500. As the implant 100 affixed to the inserter 500 is moved along the distractor/inserter rail/groove interconnection 480, the endstop 462 eventually contacts the distractor 400 (the rail 406, for example) preventing further advancement of the inserter 500 and thus preventing further advancement of the implant 100. In another embodiment, an endstop 462 may be provided on both the distractor 400 and the inserter 500. In yet another embodiment, the endstop 462 may be adjustable. It may be positionally adjustable along the length and/or width of the distractor 400 or inserter 500. It may, in another embodiment, be extendably adjustable to increase/decrease the amount the endstop 462 extends from the surface of the distractor 400 or inserter 500. These adjustments permit the distractor 400 and/or inserter 500 to be adapted based on the size of the implant 100 to be inserted. The use of the endstop 462 assures that the travel of the inserter 500 along the distractor/inserter rail/groove interconnection 480 will not permit the affixed implant 100 to travel beyond the desired midline location. The endstop 462 thus assures that the central axis of the implant 100 is properly docked at the desired location within the disc space 22. In another embodiment, the motion limiter 460 is in the form of one or more markings 464 placed on the distractor 400, inserter 500 and/or implant 100. The distractor 400 may, for example, have a marking 464a while the inserter has a marking 464b. In this case, as the implant 100 affixed to the inserter 500 is moved along the distractor/inserter rail/groove interconnection 480, the surgeon watches the relative position of the markings 464a, 464b. Once the markings 464a, 464b are aligned, the surgeon knows that the implant 100 is properly docked at the desired location within the disc space 22 and that further movement along the distractor/inserter rail/groove interconnection 480 is unnecessary. The marking 464 can take any form chosen with sound engineering judgment. It may be. for example, added onto the surface of the component. In another embodiment, it may be an etching made into the component surface(s). In yet another embodiment, the marking 464 may be colored to make it easy for the surgeon to see when the appropriate positioning of the implant 100 has been achieved.

With reference now to FIGS. 3-7, 11, and 14-16, a cable 150 (FIGS. 11 and 15) may be used to deploy or otherwise adjust the implant 100. Examples of using a cable 150 to deploy an implant are described in previously noted U.S. patent application Ser. No. 11/236,068. In one embodiment, the inserter 500 is functionally integrated with the cable 150 to simplify the required surgical technique. The functional integration may be achieved with the use of a cable attachment device 160 whereby the cable 150 can be attached to the inserter 500. The cable attachment device 160, in one embodiment, is simply a portion of the inserter 500 that the cable 150 can be attached to. This attachment may be a fixed attachment, such as where the cable can be "tied off" or otherwise fixedly connected to the inserter 500. The attachment may alternatively permit relative motion such as a pivotal connection to the inserter 500. The inserter 500 may have an opening or channel 530 that receives the cable 150 and permits the cable 150 to extend at least partially through the inserter 500. In one embodiment, shown in FIG. 15, the channel 530 is formed in the body member 524. The inserter 500, in another embodiment, may have a removable cap 532 that permits access to an internal portion of the inserter 500 so that the cable 150 can be pulled through the inserter 500 and attached to the inserter 500. The cap 532 may be attached to the proximal end of the inserter handle 540, as shown, in any manner chosen with sound engineering judgment. In one embodiment the cap 532 has one or more internal threads that are received by corresponding threads on the inserter handle 540. This provides for a secure connection. Once the cap 532 is attached to the inserter handle 540, a mallet (no( shown) may be used to advance the inserter 500 further along the distractor/inserter rail/groove interconnection 480. In another embodiment, the cap 532 has a recessed female portion in its center that can be affixed to a slap hammer (not shown) having a male threaded portion. The slap hammer has a longitudinal shaft along which a weighted cylinder with a central bore can slide to transfer forces to the inserter 500 to advance the implant 100 along the distractor/inserter rail/groove interconnection 480. Both mallets and slap hammers are well known devices to those of skill in general orthopaedic surgery and spine surgery. In yet another embodiment, the inserter may have a cutting device (not shown) for use in cutting the cable 150. The cable 150 may be cut to facilitate removal of the cable 150 from within the disc space 22 and implant 100. The cutting device can be of any type chosen with sound engineering judgment.

With continuing reference to FIGS. 3-7, 11, and 14-16, in cases where a cable 150 is used with the implant 100, it may be desirable to apply tension to the cable 150. In one embodiment, this may be accomplished by attaching the cable 150 to the inserter 500, as described above, and then moving the inserter 500 away from the implant 100. In another embodiment, it may be desirable to apply tension to the cable 150 without relative motion of the inserter 500. This may be accomplished with the use of a cable tensioning device 170 that may be positioned on or within the inserter 500. In one embodiment, the cable tensioning device 170 comprises a tensioning knob 172 that can be moved to adjust the tension on the cable 150. In one specific embodiment, the tensioning knob 172 can be rotated to adjust the cable tension. The cable tensioning device 170 may also include a rotatable shaft 174 that can be rotated by the tensioning knob 172 and about which the cable 150 can be wound. The tensioning knob 172 may extend laterally from the inserter 500, as shown. The tensioning knob 172 may, in one embodiment, be ratcheted so that successive turns of the knob 172 increase the tension on the cable 150. This increased tension, in one embodiment, applies torsional loads to the posts 104 of the implant 100, thereby forcing the implant limbs 114, 116 apart (compare FIG. 4 to FIG. 5) thereby deploying the implant 100 into its expanded state. In another embodiment, the cable tensioning device 170 may include an axle/cam mechanism (not shown). The surgeon may choose from a series of suture or cabling materials that have diameters allowing passage through the inserter 100 and the cable receiving holes 107 in the implant 100. Each of these materials has an intrinsic tensile strength with differing loads to failure. In one embodiment, the tensioning device 170 may be calibrated to match the various tensile strengths of the suture/cabling material. In a more specific embodiment, the tensioning knob 172 may be designed to provide audible sounds, "clicks" for example. As the tensioning knob 172 is rotated, it may provide a first audible sound that signifies that the implant 100 has been deployed. As the tensioning knob 172 is rotated further, it may provide a second audible sound that signifies that the cabling material is about to fail.

With reference now to all the FIGURES, the basic surgical technique for placing the implant 100 into the intradiscal space 22 between two adjacent vertebral bodies 12, 14 using the surgical instrumentation 300 of this invention will now be described. With this invention the intradiscal space 22 may be approached using universally accepted methods for antero-lateral, posterior, or posterolateral (transforaminal) discectomy. Assuming a standard approach to the posterior/posterolateral annulus of the targeted disc, appropriate retraction of the neighboring neural structures is accomplished with universally available nerve root retractors. For a posterior/posterolateral approach this would include retraction of the dural sac towards the midline and retraction of the adjacent cephalad and caudad nerve roots, as would normally be done for routine discectomy. Upon isolating the annular surface of the targeted disc, variable needle sounds are placed in the intradiscal space 22 with a range of radii of curvature. The range of these sounds would have been selected on the basis of preoperative templating of available imaging studies, including plain radiographs, CT or MRI imaging. This preoperative templating provides a narrower range of radii for intraoperative confirmation, decreasing trial and error sounding. The objective of this intraoperative needle sound placement is to locate the center of the intradiscal space 22. The placement of this sound would be confirmed via biplanar intraoperative fluoroscopic imaging. Once the surgeon is satisfied with the centralization of the needle tipped sound, routine discectomy is carried out using universally accepted instruments. The intradiscal space 22 is then initially distracted with short, straight interbody spacers, progressively sized until sufficient annular tension is achieved. Once this point is reached, longer, variable radii, curvilinear box chisels may be advanced into the intradiscal space 22 to remove disc material and cartilaginous endplate. Once a majority of intradiscal material is removed, an endplate cutter may be advanced to the entry point to make graduated cuts in the periphery of the endplate to remove the normal concave tapering of the bony endplate towards the periphery of the vertebrae. This process would insure true distraction of the intradiscal space 22 from the center.

Still referring to all the FIGURES, once the appropriate distractor 400, inserter 500 and implant 100 are selected, the distal end 402 of the distractor 400 is placed within the intradiscal space 22 and distraction to the selected level of annular tension is achieved. The degree of this distraction would be based on surgeon preference and/or the intradiscal space 22 height of neighboring non-degenerative discs. With this optimal distraction, further discectomy. or removal of disc material, may be accomplished. The distal end 402 of the distractor 400 is then placed at the presumed center of the intradiscal space 22 and centralized placement confirmed by intraoperative fluoroscopic imaging. Adjustments, if necessary, may be made in anterior-posterior and medial-lateral orientation until centralization of the distractor 400 is confirmed.

With continuing reference to all the FIGURES, the implant 100 is then affixed to the inserter 500. In one embodiment, this is achieved with the inserter/implant concave/convex interconnection 120. In one specific embodiment, the convex surface 102 formed on the implant 100. such as the post 104, is positioned within the concave surface 508 formed in the proximal end 504 of the inserter 500. If the adjustment mechanism 110 is used, it can be operated to tighten the connection of the concave surface 508 to the convex surface 102. If the implant 100 includes a cable 150, the cable 150 may be attached to the inserter 500 as described above. The implant 100 is then placed at the proximal end 404 of the distractor 400 and the inserter 500 is placed into the distractor/inserter rail/groove interconnection 480. In one specific embodiment, the inserter 500 is positioned near the proximal end of the distractor rail 406 and the inserter groove 506 is positioned to receive the rail 406. If a distractor/implant rail/groove interconnection 140 is used, the implant 100 is placed into it. In a specific embodiment, the implant 100 is positioned near the proximal end of the distractor rail 406 and the implant groove 506 is positioned to receive the rail 406.

Still referring to all the FIGURES, the inserter 500 is then moved along the distractor/inserter rail/groove interconnection 480 to move the implant 100 from the proximal end 404 of the distractor to the distal end 502 of the distractor 400. If a distractor/implant rail/groove interconnection 140 is used, the implant 100 is simultaneously moved along it. If the distractor 400 includes a curvilinear shape at the distal end 402 and a substantially linear shape at the proximal end 404. this movement includes moving the inserter 500 and implant 100 along a substantially linear path and then moving them along a curved path. If the inserter 500 includes a counter rotation handle 550, the surgeon may use it at any time to maintain the inserter 500 and implant 100 along the desired path and at the desired orientation. The implant 100 is then inserted within the disc space 22. If a motion limiter 460 is used, the surgeon may use it, as described above, to properly dock or locate the implant 100 at the desired location within the disc space 22. Biplanar fluoroscopic imaging may be used to confirm placement of the distractor 400 and full seating of the implant 100. Adjustments, if necessary, can be made at this time by adjusting the amount of distraction and/or orientation of the distractor 400 in the axial or frontal planes. If the implant 100 includes a cable 150 requiring tension, such as to deploy the implant 100, the cable tensioning device 170 is employed to apply tension to the cable 150, as described above. At this point, confirmation of satisfactory implant 100 alignment within the intradiscal space 22 may be confirmed by intraoperative biplanar fluoroscopic imaging. Adjustments, if necessary, can be made at this time by changing the degree of distraction and medial-lateral and anterior-posterior translation of the implant 100 by impaction/retraction or rotation with the inserter 500 still in place. Once satisfactory implant 100 alignment is achieved, the inserter 500 is disengaged from the implant 100 such as by loosening the connection of the concave surface 508 to the convex surface 102 with the adjustment mechanism 110. If necessary, the cutting device can be used to cut the cable 150. The inserter 500 is then moved along the distractor/inserter rail/groove interconnection 480 from the distal end 402 of the distractor to the proximal end 404 of the distractor 400 where it can then be removed. The distractor 400 is then removed from the disc space 22. With the implant 100 now inserted, bone grafting is completed by packing in the open profile of the implant 100.

With reference to all the FIGURES, all the implant embodiments may be formed of any material that is appropriate for insertion into an intradiscal space, including, but not limited to metal, metal alloy, titanium, titanium alloy, ceramic, carbon-fiber, PEEK or any other osteobiologic or inert, biocompatible material. All the distractor and inserter embodiments may be formed of any biocompatible material suitable for surgical instruments.

Numerous embodiments have been described, hereinabove. It will be apparent to those skilled in the art that the above methods and apparatuses may incorporate changes and modifications without departing from the general scope of this invention. It is intended to include all such modifications and alterations in so far as they come within the scope of the appended claims or the equivalents thereof.

We claim:

1. Surgical instrumentation for use in placing an implant into a disc space between a pair of spinal vertebrae comprising:
    a distractor having a proximal end and a distal end that may be placed into the disc space between the pair of spinal vertebrae;
    an inserter for use in moving the implant toward the disc space between the pair of spinal vertebrae;
    a distractor/inserter rail/groove interconnection that interconnects the distractor and the inserter for relative movement thereby;
    a cable that is operatively connected to the implant and that extends at least partially through the inserter; and,
    a cable tensioning device supported to the inserter and operable to apply tension to the cable to cause the implant to deploy.

2. The surgical instrumentation of claim 1 wherein the cable tensioning device comprises:
    a tensioning knob that can be moved to adjust the cable tension.

3. The surgical instrumentation of claim 2 wherein the tensioning knob is rotatable to adjust the cable tension.

4. The surgical instrumentation of claim 3 wherein:
the tensioning knob, when rotated a first predetermined amount, provides a first audible sound signifying that the implant has been deployed; and,
the tensioning knob, when rotated a second predetermined amount, provides a second audible sound signifying that the cable material is about to fail.

5. The surgical instrumentation of claim 3 wherein the cable tensioning device further comprises:
a rotatable shaft that can be rotated by the tensioning knob and about which the cable can be wound.

6. The surgical instrumentation of claim 1 wherein the inserter comprises:
an inserter handle that is attachable to a proximal end of the inserter;
a distal end that is used to contact the implant; and,
a counter rotation handle extending from the proximal end.

7. The surgical instrumentation of claim 1 wherein:
the implant has a convex surface;
the inserter has a concave surface that receives the convex surface; and,
the surgical instrumentation further comprises: an adjustment mechanism that is adjustable to tighten the concave surface of the inserter against the convex surface of the inserter.

8. Surgical instrumentation for use in placing an implant having a convex surface into a disc space between a pair of spinal vertebrae comprising:
a distractor having a proximal end and a distal end that may be placed into the disc space between the pair of spinal vertebrae;
an inserter for use in moving the implant toward the disc space between the pair of spinal vertebrae, wherein the inserter has a concave surface that receives the convex surface of the implant;
a distractor/inserter rail/groove interconnection that interconnects the distractor and the inserter for relative movement thereby; and,
an adjustment mechanism comprising a slot formed in the inserter and a sleeve that is movable with respect to the inserter to compress the slot to tighten the concave surface of the inserter against the convex surface of the inserter.

9. The surgical instrumentation of claim 8 wherein:
the slot is formed on a distal end of the inserter; and,
the sleeve is movable along the length of the inserter to compress the slot to tighten the concave surface of the inserter against the convex surface of the inserter.

10. The surgical instrumentation of claim 9 wherein the width of the inserter is tapered with the distal end being wider.

11. The surgical instrumentation of claim 10 further comprising:
a cable that is operatively connected to the implant and that extends at least partially through the inserter; and,
a cable tensioning device supported to the inserter and operable to apply tension to the cable to cause the implant to deploy.

12. The surgical instrumentation of claim 11 wherein:
the distractor comprises a first marking;
the inserter comprises a second marking; and,
the first and second markings when aligned define a motion limiter used to limit the relative movement of the distractor and the inserter along the distractor/inserter rail/groove interconnection.

13. The surgical instrumentation of claim 8 wherein the distractor/inserter rail/groove interconnection comprises:
at least one groove having at least a first relatively outer width and a second relatively inner width that is substantially greater than the first relatively outer width; and,
at least one rail that is received within the groove, the rail having a at least a first relatively outer width and a second relatively inner width that is substantially smaller than the first relatively outer width.

* * * * *